United States Patent
Gee et al.

(10) Patent No.: US 9,744,809 B2
(45) Date of Patent: Aug. 29, 2017

(54) ENHANCED SOUND GENERATION FOR QUIET VEHICLES

(71) Applicant: Continental Automotive Systems, Inc., Auburn Hills, MI (US)

(72) Inventors: Robert Allen Gee, Lake Barrington, IL (US); Shafer Burch Seymour, Bartlett, IL (US)

(73) Assignee: Continental Automotive Systems, Inc., Auburn Hills, MI (US)

( * ) Notice: Subject to any disclaimer, the term of this patent is extended or adjusted under 35 U.S.C. 154(b) by 0 days.

(21) Appl. No.: 14/933,819

(22) Filed: Nov. 5, 2015

(65) Prior Publication Data

US 2017/0129397 A1    May 11, 2017

(51) Int. Cl.
| | |
|---|---|
| *B60C 5/00* | (2006.01) |
| *B60K 28/06* | (2006.01) |
| *A61B 5/08* | (2006.01) |
| *B60W 40/08* | (2012.01) |

(52) U.S. Cl.
CPC .............. *B60C 5/008* (2013.01); *A61B 5/082* (2013.01); *B60K 28/066* (2013.01); *B60W 40/08* (2013.01); *B60W 2040/0818* (2013.01); *B60W 2540/26* (2013.01)

(58) Field of Classification Search
CPC . B60Q 1/525; B60Q 1/22; B60Q 5/00; G60Q 5/008; A61B 5/082; B60K 28/066; B60W 40/08; B60W 2040/0818; B60W 2540/26
See application file for complete search history.

(56) References Cited

U.S. PATENT DOCUMENTS

| | | | |
|---|---|---|---|
| 5,465,079 A * | 11/1995 | Bouchard | G01S 13/325 180/272 |
| 5,691,693 A | 11/1997 | Kithil | |
| 6,580,973 B2 * | 6/2003 | Leivian | B60R 16/0231 701/1 |
| 7,777,619 B2 * | 8/2010 | Yopp | B60K 28/066 180/272 |
| 9,081,650 B1 * | 7/2015 | Brinkmann | G07C 5/008 |
| 9,104,535 B1 * | 8/2015 | Brinkmann | B60W 40/09 |
| 9,290,174 B1 * | 3/2016 | Zagorski | B60K 28/06 |
| 2002/0151297 A1 * | 10/2002 | Remboski | B60R 16/0231 455/414.1 |
| 2004/0088095 A1 * | 5/2004 | Eberle | B60K 28/02 701/45 |

(Continued)

FOREIGN PATENT DOCUMENTS

| | | |
|---|---|---|
| JP | 2001219760 A | 8/2001 |
| JP | 2011150577 A | 8/2011 |

OTHER PUBLICATIONS

Search Report dated Jul. 21, 2016, from corresponding GB Patent Application No. GB1602424.2.

(Continued)

*Primary Examiner* — An T Nguyen

(57) ABSTRACT

The presence of an electrically-powered quiet vehicle is accomplished by determining a state of mind or physical state of the driver, determining the presence and proximity of humans and other objects, how the vehicle is being operated and generating a noise correlative to the threat posed by the vehicle to humans and other objects.

12 Claims, 2 Drawing Sheets

(56) References Cited

U.S. PATENT DOCUMENTS

| | | | |
|---|---|---|---|
| 2007/0182529 A1* | 8/2007 | Dobler | B60K 28/06 340/438 |
| 2008/0106908 A1* | 5/2008 | Englander | B60Q 1/24 362/481 |
| 2008/0204256 A1* | 8/2008 | Omi | G08B 21/06 340/575 |
| 2009/0160678 A1* | 6/2009 | Turnbull | B60Q 1/525 340/944 |
| 2009/0292528 A1* | 11/2009 | Kameyama | G08G 1/0962 704/9 |
| 2011/0121960 A1* | 5/2011 | Tsai | B60K 28/06 340/439 |
| 2012/0095646 A1* | 4/2012 | Ghazarian | G01S 19/17 701/36 |
| 2012/0130580 A1* | 5/2012 | Omote | G10K 15/02 701/22 |
| 2013/0009768 A1* | 1/2013 | Terao | B60Q 5/008 340/463 |
| 2013/0144474 A1* | 6/2013 | Ricci | G06F 9/54 701/22 |
| 2014/0097957 A1 | 4/2014 | Breed et al. | |
| 2014/0104405 A1* | 4/2014 | Weidl | A61B 5/02416 348/77 |
| 2014/0135598 A1* | 5/2014 | Weidl | A61B 5/6893 600/301 |
| 2014/0221781 A1* | 8/2014 | Schrauf | A61B 5/0205 600/301 |
| 2015/0035685 A1* | 2/2015 | Strickland | B60Q 9/008 340/901 |
| 2015/0269829 A1* | 9/2015 | Birnie | G08B 21/06 340/575 |
| 2016/0272215 A1* | 9/2016 | Laine | B60W 50/14 |

OTHER PUBLICATIONS

English translation of abstract of JP2011150577A.
English translation of abstract of JP2001219760A.

* cited by examiner

ENHANCED SOUND GENERATION FOR QUIET VEHICLES

BACKGROUND

Battery powered and hybrid electric vehicles are quiet, i.e., other than tire noise, they emit almost no sound when they travel over a roadway. While such vehicles are fuel efficient and their reduced operating noise levels generally considered desirable, many pedestrians, cyclists and drivers of other types of vehicles are somewhat conditioned to listen for the usual engine sounds of an internal combustion engine to determine whether a vehicle is approaching. When the sound of a conventionally-powered vehicle is not heard, pedestrians and other drivers often mistake the absence of such noise as an indication that no vehicles are approaching or nearby. Stated another way, quiet vehicles can sometimes be dangerous because of their quiet drive trains. Moreover, the safety hazard presented by quiet vehicles can be exacerbated when the driver of such a vehicle is physically or mentally impaired or distracted. A method and apparatus for enunciating or announcing the approach or presence of a quiet vehicle operated by an impaired driver would be an improvement over the prior art.

DETAILED DESCRIPTION

For purposes of clarity, as used herein, the term, "quiet vehicle" refers to a motor vehicle propelled by one or more electric motors. The term thus includes hybrid-electric vehicles like the Toyota® Camry® and electric cars, like the entirely battery-powered Nissan® Leaf®.

The term, "real time" refers to the actual time during which something takes place.

Noise is generally considered to be an undesirable sound or signal. As used herein, the term "noise" refers to an audible sound that attracts attention. A generated noise can thus be an audible sound that is generated with or without an agreeable musical quality or one that is either noticeably pleasant or unpleasant.

Figure 1:
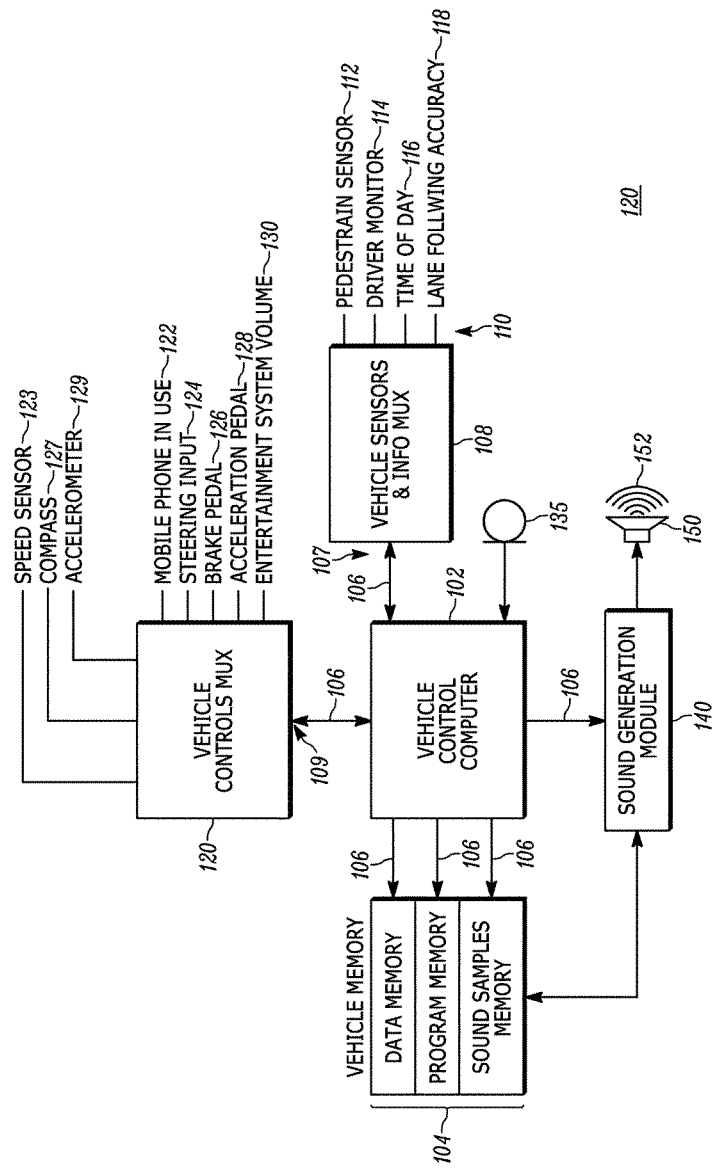
FIG. 1 is a block diagram of an apparatus for announcing the presence of a quiet vehicle responsive to a driver's impairment.

A multiplexer is an electronic device that selects one input signal from a number of input signals and switches or routes the information at or from a particular input to a single output FIG. 1 is a block diagram of an apparatus 100 for announcing the approach or presence of a quiet vehicle, the nature of the vehicle's announcement by the apparatus 100 being dependent upon or responsive to a driver's impairment level or degree and whether there are pedestrians, cyclists, other vehicles and other objects nearby. The apparatus 100 comprises a computer 102 operatively coupled to a non-transitory memory device or devices 104 via a conventional bus 106, which is a set of electrically parallel conductors in a system that forms a main transmission path. In addition to being coupled to memory devices 104, the computer 102 is coupled to a first conventional multiplexer 108. The single output 107 of the multiplexer 108 can thus provide to the computer 102, various signals 110 input to the multiplexer inputs from multiple different types of sensors, not shown but well known to those of ordinary skill in the art and therefore omitted in the interest of brevity.

A first sensor is a pedestrian sensor 112. It is coupled to the first multiplexer 108 and detects the presence of a human in front of or adjacent a motor vehicle by measuring one or more characteristics of a human, such as shape and surface temperature. One such sensor is available from Neurotechnology, which is a company located at Laisves Ave. 125A Vilnius, LT-06118, Lithuania. Such a sensor is also described in a publication available on line at http://www.prnewswire.com/news-releases/verilook-surveillance-30-sdk-identifies-faces-and-moving-objects-differentiates-pedestrians-from-other-moving-objects-in-video-surveillance-systems-279250992.html, which is incorporated herein by reference. See also, Shinya Saito and Takeki Ogitsu, "Face Detection-based System to Sense Pedestrians At High Risk of Collision," I.E.E.E. Computer Society, 2015, 6th International Conference on Intelligent Systems, Modelling and Simulation, pages 21-23, also incorporated herein by reference.

Distances between a vehicle and a detected human, cyclist, motor vehicle or other object can be measured using RADAR, SONAR or LIDAR, a prior art remote sensing technology that measures distance by illuminating a target with a laser and analyzing the reflected light, all of which are part of the pedestrian sensor.

The pedestrian sensor 112 detects humans and provides signals indicating the presence of pedestrians, i.e., whether a human is walking, cyclists riding on motor-driven bicycles, cyclists riding on pedal-powered bicycles and provides signals that indicate the direction of their travel, including the direction that a curb-side pedestrian is facing, and the distance between them and a vehicle, in real time. A plurality of such pedestrian sensors 112 distributed around the vehicle and directed away from the vehicle in different directions enables the detection of pedestrians as they approach the vehicle from different directions as well as an approach of the vehicle toward a stationary pedestrian, in real time.

As used herein, the term "vital signs" refers to the pulse rate, respiratory rate, body temperature, and often blood pressure of a person. Driver monitors 114 measure a driver's pulse, respiration rate, body temperature, eye movement and head movement and provide quantitative information indicative of a driver's health, fatigue or agitation level and thus a quantitative measure of the driver's level of physical and mental impairment. Being coupled to the first multiplexer 108, the vital signs sensors can provide a driver's vital data to the computer 102 for analysis.

A clock 116 or time of day sensor provides data representing the actual time of day when various events occur or conditions are detected, including their duration. Occurrences of various events and detections of various conditions, and their durations, are stored as the time they begin and the time at which they end, in the data portion of the vehicle memory 104 and thus enable historical analyses of events and conditions over time.

A lane sensor 118, also known in the art, detects when a vehicle drifts or crosses a lane line in real time and provides a signal indicative thereof to the multiplexer 108.

Signals from the various sensors provided to the multiplexer 108 are provided there through to the computer 102 via the bus 106, responsive to control signals sent to the multiplexer 108 from the computer 102. Stated another way, the computer 102 selects which sensor information to "read" by way of control signals sent to the multiplexer 108 from the computer 102 via the bus 106. The computer 102 is thus able to selectively detect humans, detect vehicles and other objects around the vehicle, measure distances between the vehicle and humans, vehicles and objections, sense various operations of the vehicle's control systems by the driver in real time, measure one or more "vital signs" of the driver in real time and compare the driver's real-time vital signs to various real-time operations of the vehicle's driving controls by the driver. Stated another way, the computer 102 is provided with information by which the computer 102 can determine whether the vehicle's quiet operation might present a safety threat to a human, a vehicle or other object in its path.

Monitoring the driver's operation of the vehicle, i.e., the driver's physical manipulation of the vehicle's controls is accomplished by way of a second multiplexer referred to herein as a vehicle controls multiplexer 120 to which various vehicle operation sensors are coupled. As with the first multiplexer, the second multiplexer has a single output 107B and several inputs, each of which is coupled to a different sensor for various vehicle controls.

One vehicle control sensor is a mobile telephone or cell phone use detector/sensor 122. It provides signals to the second multiplexer 120 indicating whether a cell phone in the vehicle is in use. Cell phone use includes a conversation, text messaging, Internet browsing, playing back multimedia files and composing or reading e-mail messages.

A steering control input sensor 124 provides signals to the multiplexer 120 indicating the driver's operation of the vehicle's steering wheel, i.e., movement of the steering wheel around its axis of rotation. Signals from the steering control input sensor 124 can indicate whether the driver is correcting or changing the vehicle steering wheel position too quickly or excessively for the speed at which the vehicle is moving.

A brake pedal operation sensor 126, an accelerator pedal operation sensor 128 and an entertainment system volume sensor 130 provide corresponding signals indicative of the driver's brake pedal usage, accelerator pedal usage and the level or volume of audio output from the vehicle's infotainment system.

A vehicle speed sensor 123, a compass 127 and an accelerometer 129 provide corresponding information-bearing signals to the vehicle controls multiplexer 120. Data from those sensors 123, 127, 129 enable the computer 102 to know or determine the vehicle's speed, direction or travel, whether the vehicle is turning, accelerating or decelerating, all in real time.

As with the vehicle sensor information multiplexer 108 the vehicle's second multiplexer 120 provides signals received by it from the various vehicle sensors to the computer 102, in real time, via signals sent to the second multiplexer from the computer 102 via the bus 106. The computer 102 is thus able to selectively obtain information-bearing signals in real time, which are indicative of the driver's operation of the vehicle, including the driver's operation of a wireless communications device inside the vehicle. Sensor information provided to the first multiplexer 108 can thus be correlated to a driver's operation of a vehicle, as indicated by sensor information provided to the second multiplexer 120. A driver's operation of the vehicle can thus be correlated to the driver's mental and physical state or level of impairment.

As described below, the computer 102 is configured to read and execute program instructions stored in the non-transitory memory device 104, which when executed cause the computer 102 to read various signals from various sensors and quantitatively determine the degree or level by which the driver might be impaired physically or mentally. Stated another way, the computer 102 executes program instructions from memory 104, which enable the computer 102 to determine in real time the driver's state of mind or physical state from real-time measurements of one or more vital signs of the driver and real-time measurements of the driver's usage or operation of the vehicle driving controls responsive to the presence or absence of humans, vehicles or other objects in front of or near the vehicle, whether the vehicle is moving or stationary. The computer 102, its programming stored in memory 104 and the various sensors described above are thus considered to be a driver impairment determiner inasmuch as they are able to quantitatively measure a driver's state of mind and physical state, i.e., wellbeing.

Referring again to FIG. 1, a conventional microphone 135 is sized and arranged or "configured" to transduce sound waves outside the vehicle into measurable electrical signals. Electrical signals from the microphone are processed by the computer 102 to provide a Fast Fourier analysis of ambient noise. Stated another way, the microphone 135 enables the computer 102 to sample audio signals, i.e. ambient noise or noise outside the vehicle, and provide a numeric representation of frequency and magnitude of various audio frequency components that make up or comprise the ambient noise.

In a preferred embodiment, program instructions inside the memory device 104 cause the vehicle computer 102 to generate an audio output signal embodied as one or more audio-frequencies, and provide such an audio signal to a sound generation module 140. The sound generation module 140 provides an alternate current (A.C.) signal to a conventional loudspeaker 150, which is simply an audio signal transducer. The characteristics of the generated audio noise signals are such that the signals 152 emitted from the 150 are made to be as distinguishable as possible.

The frequencies generated by the computer 102 and their amplitudes are selected by program instructions in order to make the generated noise as distinguishable from ambient noise as might be possible but the selection of noise signal frequencies and noise signal frequency amplitudes also considers a driver's level of impairment. By generating audio frequency signals at amplitudes not found in the ambient noise, the generated noise 152 from the loud speaker is thus preferentially audible to pedestrians and vehicle drivers that might be proximate to the vehicle when the vehicle is being driven by an impaired driver. By selecting frequencies of a signal according to a driver's physical or mental state, pedestrians and other drivers can also be made aware of a driver that might be a serious threat to their safety.

In the preferred embodiment, characteristics of the generated noise are selected under software control based upon the computer's determination of the driver's state of mind or physical state and those frequencies are adjusted to improve the likelihood that the impaired driver will be announced to pedestrians, cyclists and drivers of other motor vehicles nearby.

In an alternate embodiment, digitized music and other types of sounds are stored as corresponding data files in the data memory portion of the vehicle memory 114. The vehicle's horn can also be used as a noise source.

Sounds stored in the vehicle memory 114 are selected for playback by the computer 102, according to varying needs to enunciate a quiet vehicle's presence, e.g., a driver's level of impairment and how the impaired driver is operating the vehicle. In such an alternate embodiment, sounds stored in the vehicle memory 114 are selected for playback by the computer 102 responsive to one or more of a driver's impairment level, the presence of pedestrians, cyclists, other vehicles and other objects, but also responsive to the vehicle's speed and the driver's operation of it.

Figure 2:
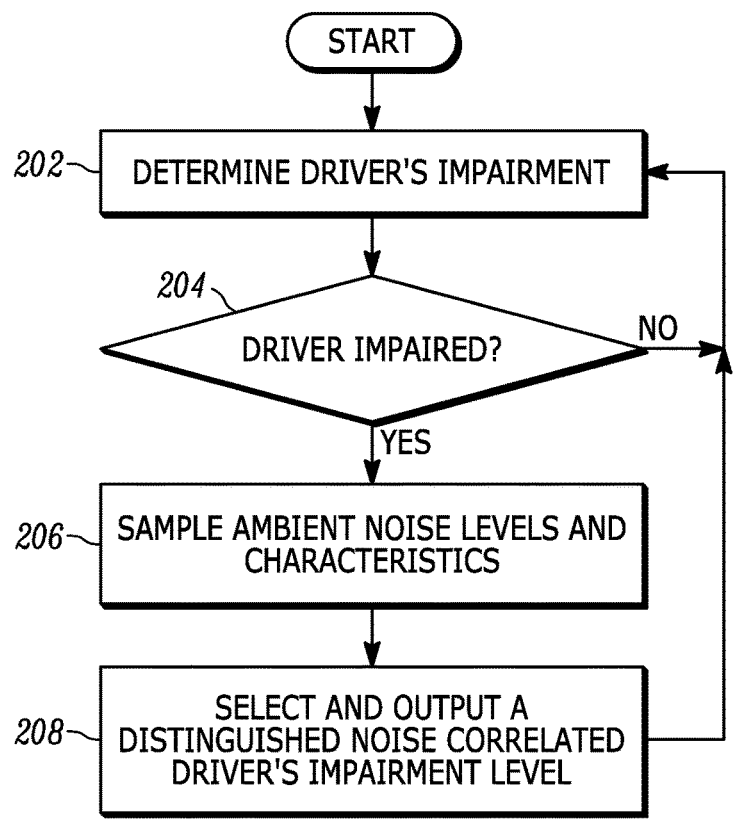
FIG. 2 is a flowchart depicting steps of a method for announcing the presence of a vehicle operated by a driver, the announcement being dependent upon the level of impairment of a driver.

FIG. 2 depicts steps of a preferred method of announcing the presence of a vehicle operated by a driver who might be impaired. At a first step 202 a driver's level of impairment, if any, is determined by reading signals from various vital signs sensors described above. At step 204, a decision is made whether the driver might be impaired based upon a comparison of the signals obtained from the driver's vital sign sensors to a baseline value of each sensor stored in the vehicle memory device 104, as well as a historical record of vital signs stored in the vehicle memory 104. If the driver is not determined to be impaired, the method 200 continues looping through steps 202 and 204 until driver impairment is detected, there being no reason to enunciate the quiet vehicle if the driver is fully functional. The driver's impairment level is thus monitored in real time continuously or nearly continuously.

At step 206, which occurs after determining that the driver might impaired, ambient noise levels are sampled and their frequency and amplitude characteristics determined using conventional Fourier analysis, well-known to those of ordinary skill in the digital signal processing art. Other extrinsic circumstances and conditions are also considered at step 206. Such other circumstances and conditions include but are not limited to the vehicle's speed, direction, acceleration or deceleration, whether the driver is using a mobile phone, listening to music and whether there are pedestrians, cyclists, other vehicles or other objects in front of, next to or behind the vehicle.

At step 208, program instructions stored in the memory device 104 cause the computer 102 to select and generate audio frequency signals responsive to a computer-determined level of threat that the quiet vehicle poses to pedestrians, cyclists, other vehicles or other objects in front of, next to or behind the vehicle. The noise or sound to produce, including those stored in and selected from the vehicle memory 104 are selected such that they are more readily detected by a pedestrian or vehicle driver. Such signals are identified by selecting sounds having frequencies and output amplitudes different from the ambient noise and correlated to the real-time level of threat posed by the driver's current level of impairment and the driver's current operation of the vehicle.

Figure 3:
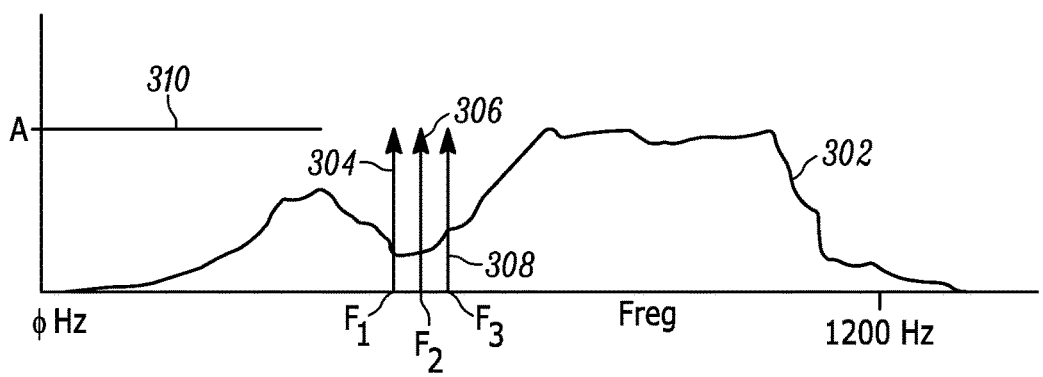
FIG. 3 depicts a plot of an audio frequency spectrum of ambient noise and depicts three different frequency-signals, the frequencies and amplitudes of which are selected to be distinguishable from the ambient noise.

FIG. 3 depicts a graph of the ambient noise signals 302 at a particular instance of time outside a vehicle. The spectrum 302 extends from zero (0) Hertz up to about 12000 Hertz., i.e., above the frequency most humans can hear.

The ambient noise 302 between two particular frequencies identified as F1 and F2 is reduced or somewhat lower relative to the amplitudes of other frequency components of the ambient noise 302.

In the preferred embodiment, program instructions stored in the memory device 104 cause the computer 102 to generate audio frequency signals 304, 306 and 308 "located" in the relative "pass band" between F1 and F3. The amplitudes of those generated noise signals 304, 306 and 308 are provided with amplitudes 310 that are at least as large as the ambient noise level at their respective frequencies. The computer-generated frequency components 304, 306 and 308 will thus be more distinguishable or identifiable from ambient noise 302 because they are generated in or "placed into" a portion of the audio frequency spectrum where ambient noise components are lowest, relative to other signals between zero and twelve-thousand Hertz. In the alternate embodiment, wherein music or other audio is obtained from the vehicle memory 104 and generated as "noise," the amplitude of such noise is made to be at least as great as the amplitude of the ambient noise.

In view of the foregoing and for the sake of completeness and clarity, noise should be construed to include any and all forms and types of audio signals, generated by or emitted from a quiet vehicle to announce its presence or approach, including the sound emitted from the vehicle's horn. Those of ordinary skill in the art should recognize that the announcement of a quiet vehicle to pedestrians and nearby motorists when a driver is impaired, using audio frequency signals specifically selected to be detectable from ambient noise would be an improvement over the prior art. The foregoing description is thus for purposes of illustration only. The true scope of the invention is set forth in the following claims.

What is claimed is:

1. A method of announcing a presence of a vehicle operated by a driver, the method comprising:
   determining a state of mind or physical state of the driver in real time;
   determining whether a driver is impaired based upon the determined state of mind or physical state of the driver;
   when the driver is determined to be impaired:
      generating noise, audible to at least pedestrians that are proximate to the vehicle when it is being driven, characteristics of the generated noise being selected from a plurality of different characteristics responsive to a determined state of mind or determined physical state of the driver;
      sampling ambient noise from electrical signals received from a microphone;
      determining a frequency spectrum of ambient noise signals;
      identifying at least one portion of the ambient noise frequency spectrum, where the ambient noise is lowest relative to amplitudes of other component frequency signals;
      generating at least one audio frequency signal component, which is in the at least one portion of the ambient noise frequency spectrum where the ambient noise is lowest relative to amplitudes of other component frequency signals; and
      outputting the at least one audio frequency signal component that is in the at least one portion of the ambient noise frequency spectrum where the ambient noise is lowest relative to amplitudes of other component frequency signals.

2. The method of claim 1, further comprising determining a state of mind or physical state of the driver, such a determining step comprising:
   measuring at least one vital sign of the driver in real time;
   correlating the at least one vital sign with a level of driver impairment in real time; and wherein the step of generating noise comprises selecting characteristics of generated noise responsive to the driver's level of impairment.

3. The method of claim 1, wherein the step of determining a state of mind or physical state comprises:
substantially continuously measuring the driver's operation of the vehicle driving controls in real time.

4. The method of claim 1, wherein the step of determining a state of mind or physical state comprises:
determining the driver's operation of a wireless communications device.

5. The method of claim 1, wherein the step of determining a state of mind or physical state comprises:
determining the speed of the vehicle and separation of the vehicle from objects in front of the vehicle in real time;
determining the driver's operation of a plurality of vehicle operation controls in real time.

6. The method of claim 1, wherein the vehicle is quiet.

7. The method of claim 1, wherein the step of generating noise comprises:
generating audible signals from an audio signal transducer.

8. The method of claim 5, wherein the step of generating noise further comprises:
selecting the additional noise based on at least one of:
the driver's level of impairment;
the driver's operation of the vehicle;
an activity of a pedestrian, motor vehicle or other object.

9. An apparatus for announcing a presence of a vehicle operated by a driver, the apparatus comprising:
a driver impairment determiner, configured to determine in real time whether the driver is impaired based on at least one of: a driver's state of mind and physical state;
a noise generator, configured to, when the vehicle is being driven and the driver impairment determiner has determined that the driver is impaired, generate noise that is audible to at least pedestrians proximate to the vehicle, characteristics of the generated noise being selected by the noise generator from a plurality of different characteristics responsive to the determined state of mind or physical state of the driver;
wherein the driver impairment determiner comprises:
a computer;
a first plurality of sensors coupled to the computer, each sensor of the first plurality of sensors being configured to measuring at least one vital sign of the driver;
a second plurality of sensors coupled to the vehicle and to the computer, each sensor of the second plurality of sensors being configured to measuring the driver's operation of a vehicle operating control;
a third plurality of sensors, coupled to the vehicle and to the computer, each sensor of the third plurality of sensors being configured to detect a pedestrian, cyclist, vehicle or other object near the vehicle;
a non-transitory memory device operatively coupled to the computer, the memory device storing executable program instructions, which when executed cause the computer to:
read signals from the first plurality of sensors;
read signals from the second plurality of sensors; and
determine at least one of: a driver's state of mind and physical state by correlating signals that are read from the first plurality of sensors to signals that are read from the second plurality of sensors;
wherein the noise generator comprises an audio noise signal generator coupled to the computer and a loudspeaker coupled to the audio noise signal generator;
a microphone, operatively coupled to the computer, the non-transitory memory device storing additional program instructions, which when executed by the computer they cause the computer to:
sample ambient noise from electrical signals received by the computer from the microphone;
determine a frequency spectrum of ambient noise signals;
identify at least one portion of the ambient noise frequency spectrum, where the ambient noise is lowest relative to amplitudes of other component frequency signals;
generate at least one audio frequency signal component, which is in the at least one portion of the ambient noise frequency spectrum where the ambient noise is lowest relative to amplitudes of other component frequency signals; and
output the at least one audio frequency signal component that is in the at least one portion of the ambient noise frequency spectrum where the ambient noise is lowest relative to amplitudes of other component frequency signals.

10. The apparatus of claim 9, wherein the second plurality of sensors comprises: a wireless communications device operation detector, configured to detect operation of a wireless communications device inside the vehicle.

11. The apparatus of claim 9, wherein the second plurality of sensors comprise at least one of:
a steering wheel operation sensor;
a brake pedal operation sensor;
an accelerator pedal operation sensor; and
an entertainment system audible volume setting sensor.

12. The apparatus of claim 9, wherein the first plurality of sensors comprise at least one of:
a pedestrian sensor;
a driver pulse sensor;
a driver's body temperature sensor;
a driver's eye movement sensor; and
a driver's lane change detector.

* * * * *